(12) United States Patent
Järventie

(10) Patent No.: US 7,160,456 B2
(45) Date of Patent: Jan. 9, 2007

(54) METHOD AND EQUIPMENT FOR PROCESSING ORGANIC MATERIAL

(75) Inventor: Jussi Järventie, Kuhmoinen (FI)

(73) Assignee: Preseco Oy, Helsinki (FI)

( * ) Notice: Subject to any disclaimer, the term of this patent is extended or adjusted under 35 U.S.C. 154(b) by 101 days.

(21) Appl. No.: 10/514,465

(22) PCT Filed: May 20, 2003

(86) PCT No.: PCT/FI03/00390

§ 371 (c)(1),
(2), (4) Date: Mar. 22, 2005

(87) PCT Pub. No.: WO03/097560

PCT Pub. Date: Nov. 27, 2003

(65) Prior Publication Data

US 2005/0155928 A1    Jul. 21, 2005

(30) Foreign Application Priority Data

May 21, 2002  (FI)  ................................. 20020952
May 12, 2003  (FI)  ................................. 20030705

(51) Int. Cl.
*C02F 3/28* (2006.01)
*C02F 11/04* (2006.01)

(52) U.S. Cl. ...................... 210/603; 210/613; 210/631; 210/903; 210/259; 423/234

(58) Field of Classification Search ................ 210/603, 210/612, 613, 631, 903, 908, 252, 259; 71/10, 71/15, 21; 423/234
See application file for complete search history.

(56) References Cited

U.S. PATENT DOCUMENTS

| | | | |
|---|---|---|---|
| 4,302,236 A | 11/1981 | Roman | |
| 4,372,856 A * | 2/1983 | Morrison | ..................... 210/603 |
| 4,824,571 A | 4/1989 | Ducellier | |
| 5,529,692 A * | 6/1996 | Kubler | ..................... 210/603 |

FOREIGN PATENT DOCUMENTS

| | | |
|---|---|---|
| DE | 3 134 980 | 4/1983 |
| DE | 3 603 739 A1 | 8/1986 |
| DE | 3 823 950 A1 | 1/1989 |
| EP | 0 486 466 | 5/1992 |
| EP | 0 589 155 A1 | 3/1994 |
| EP | 0 818 424 A2 | 1/1998 |
| FR | 2 576 741 A1 | 8/1986 |
| WO | WO 93/06064 | 4/1993 |

* cited by examiner

*Primary Examiner*—Fred G. Prince
(74) *Attorney, Agent, or Firm*—Sughrue Mion, PLLC

(57) ABSTRACT

A method for processing organic material, in which method bioconversion is performed on the organic material in at least one first reactor, the biogas formed in the bioconversion is treated with ammonia in at least one second reactor and buffer solution produced in the second reactor is recycled to the bioconversion in the first reactor. Thus, the carbon dioxide of the mixed methane/carbon dioxide gas reacts with the ammonia and forms a buffer compound, such as ammonium bicarbonate and/or ammonium carbonate.

33 Claims, 2 Drawing Sheets

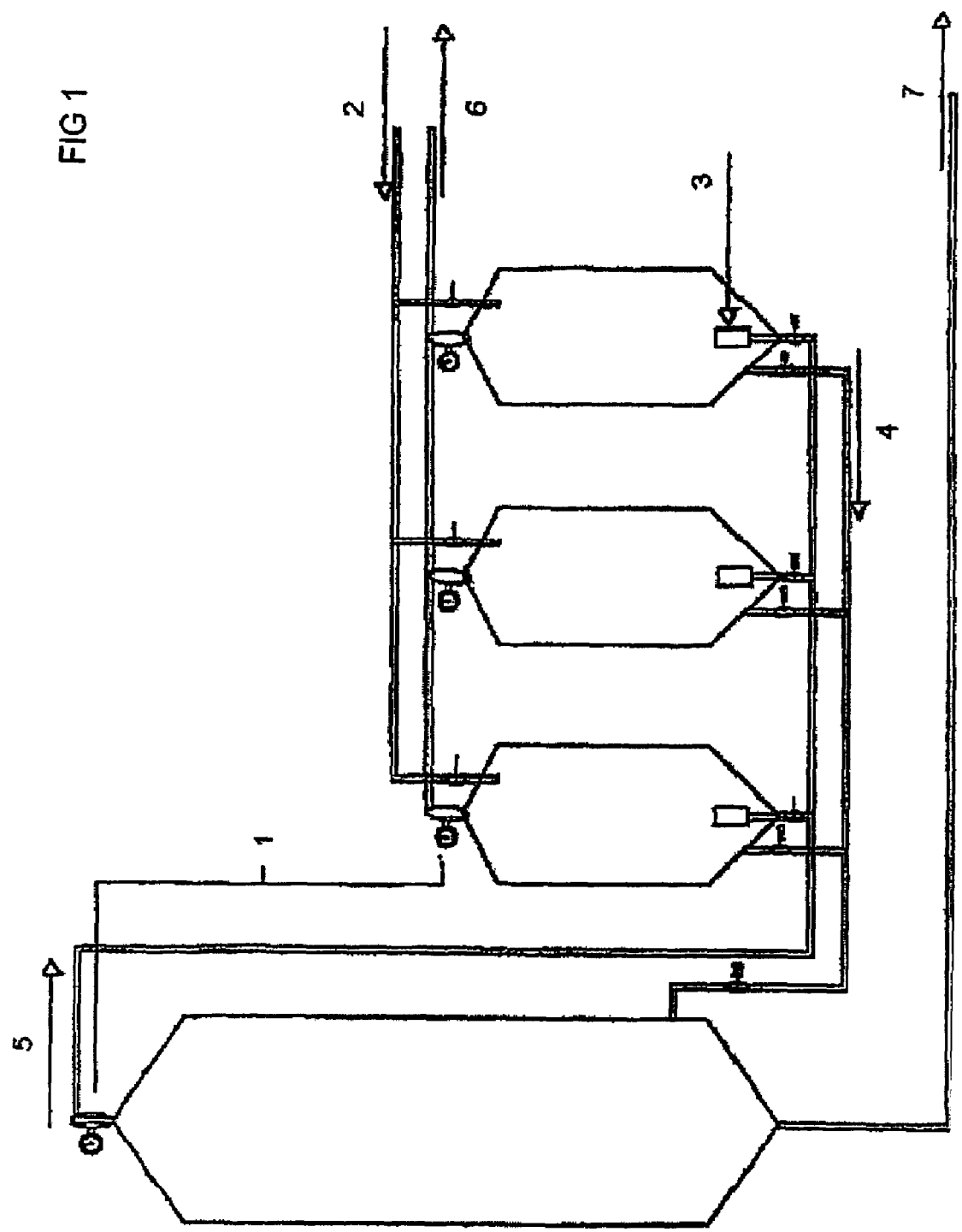

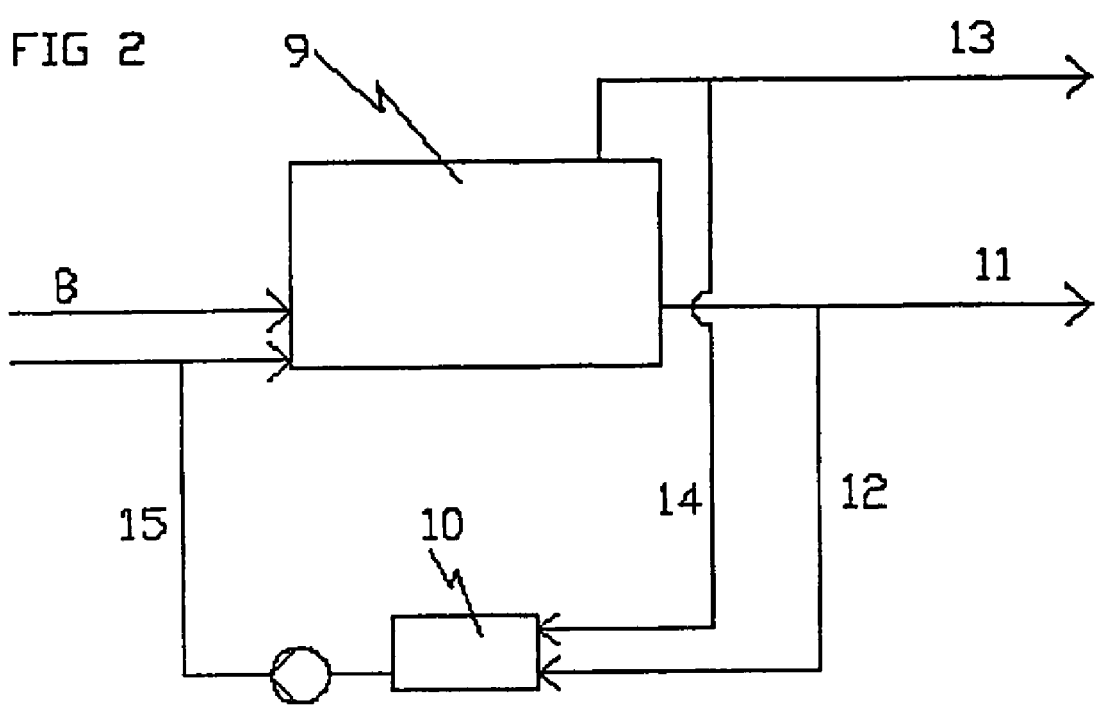

METHOD AND EQUIPMENT FOR PROCESSING ORGANIC MATERIAL

BACKGROUND OF THE INVENTION

The invention relates to a method for processing organic material and, particularly to a method, which utilizes highly ammoniacal organic material in cleaning a biogas produced in degradation, and to equipment for implementing the method. The invention also relates to products obtained by the method.

The publication U.S. Pat. No. 4,824,571 discloses a method and equipment for degradation of various organic products and wastes in an anaerobic medium. The method generates degraded products and biogas. In the method the mass to be degraded is introduced into a fermentation vat and the produced biogas is recovered. Thereafter the biogas is fed back into the vat from the bottom so as to provide a fluidization effect.

The publication U.S. Pat. No. 4,302,236 discloses a use of a composting system for scrubbing gas effluvia. In the method, inorganic acid-forming constituents are removed from a gas stream high in sulphur, in particular. Inorganic groups form inorganic acids in the presence of oxygen or water. The gas stream to be cleaned is passed through an active composting biodegradable organic waste, which is held under thermophilic bacteria-phase digestion conditions.

The publication WO 93/06 064 discloses a method for neutralizing and recovering gases formed in connection with wet composting. The object of the invention described in the publication is to render harmful, toxic and/or polluting manure gases harmless. According to the publication part of the gases is recycled to the composted mass so as to improve its nutrient value.

The publication DE 3,134,980 discloses a method for mixing biomass in oxygen-free environment in a biogas reactor by means of biogas produced by bacterial strains and stored in a biogas storage. In the method the biomass is mixed with periodic biogas blows. The necessary biogas pressure is provided by means of the bacterial strains in the biogas reactor. The reactor is externally closed and it communicates with the biogas pressure vessel. Pressure is released in the biogas pressure vessel and next it is blown into the biomass, from which the biogas is further conducted into a biogas container.

EP application 486,466 discloses a method for controlled and continuous aerobic biological decomposition of organic wastes. Decomposing material, which is optionally inoculated with a mixture of bacteria and microbes, is fed into the material in the microbiological waste and the degraded material is removed, whereby an oxygen-containing gas is passed in for the degradation. The aim of the method described in the publication is to control the degradation of nitrogen-containing products. In the method, $CO_2$ gas is added to the oxygen-containing gas, depending on the $NH_3$ content and the pH of the degradation product, whereby the gas is mixed with a fraction that contains no, or very little, nitrogen. The method described in the publication is an aerobic method.

Organic material is received from various sources from products of plant and animal origins. One problem with organic material degradation plants is that availability of material to be processed is season-dependent and within a short period of time the plant must be able to process even large amounts of organic matter solids, because they do not allow long storage. Preservation of organic material poses several problems, for instance, preservation produces $NH_3$, which is a toxic compound and prevents microbes from functioning. Currently the bioconversion reactors allow introduction of only low solids contents, because $NH_3$ prevents the microbial function in the reactors. Preservation of seasonally produced organic material also causes problems, because it cannot be preserved neither in acidic nor in basic conditions, if conventional bioconversion processes are employed, because they are sensitive to variations in the pH. Conventional bioconversion processes are also extremely sensitive to changes in temperature.

In addition, conventional processes produce biogas that is high in carbon dioxide. Carbon dioxide is a harmful compound to the environment and there is a general objective to get rid of it.

BRIEF DESCRIPTION OF THE INVENTION

It is an object of the invention to provide a method and equipment implementing the method such that the above-mentioned problems can be solved. This is achieved with a method and a system, which are characterized by what is disclosed in the independent claims. The preferred embodiments of the invention are disclosed in the dependent claims.

The invention is based on the idea that biogas is passed from a first reactor that processes a degradation process, i.e. hydrolysis, through a second, pressurized reactor, which contains ammonia or highly ammoniacal organic material. Thus the carbon dioxide in a mixed methane/carbon dioxide gas reacts in the second reactor with the ammonia forming ammonium bicarbonate and/or ammonium carbonate. The formed compound(s) constitute(s) a part of a buffer compound that does not inhibit the microbes in the process to the same extent as free ammonia, because the formed buffer compound prevents variations in the pH that are adverse to the microbes. Hence, a sludge produced in the second reactor, the sludge consisting of the mass to be hydrolyzed and the biogas and containing a buffer compound or buffer compounds, can be recycled into the first reactor.

The organic material to be processed can be of plant or animal origin. In the present document the organic material refers to any organic constituent. The highly ammoniacal material refers in this context to ammonia-containing material. The ammonia may originate either from the biowaste to be processed alone, or it can be added to the material to be processed, if necessary. In particular, organic materials rich in proteins and/or fats produce naturally large amounts of ammonia. The ammonia added to the organic material to be processed, or free ammonia produced therein by microbes, softens cell membranes in such a way that bioconversion, i.e. hydrolysis, per se also accelerates considerably. The method and equipment of the invention can be utilized both in pressurized and unpressurized bioconversion processes.

The present invention has an advantage that organic material can be preserved in basic or acidic conditions prior to the bioconversion process. This is particularly advantageous when seasonally produced waste is to be digested. Preservation with an acid or a base can be finally utilized in connection with a bioconversion process. Previously this has not been possible, because material preserved with an acid or a base cannot have been digested further. Preservation with an acid or a base also refers to the fact that the organic material can be hygienized before it is brought to bioconversion. In this connection, hygienization refers to killing the pathogenic bacteria in the material. Previously hygienization was carried out, for instance, by heat treatment, i.e. pasteurization. Thus, the system of the present invention provides an alternative to hygienization by heat treatment.

An advantage with the method and the system of the invention is that larger amounts of solid matter can be introduced into the bioconversion. In addition, microbiologically active waste can be stored in an optimal state in view of methane yield, and such that the hygienic level complies with the EU directives, without thermal manipulation. The method of the invention has an advantage that it is possible to reintroduce a buffer solution and/or buffer-solution-containing organic material to be processed into the hydrolysis reactors, which have interrupted their process due to excessive ammonia content, and they can be restarted. In addition, the method of the invention makes it possible to preserve the organic material longer than before, which facilitates the storage. The formed ammonia does no longer prevent the processing, but on the contrary, a long storage time pre-processes the waste. The method produces a hydrolysis product and biogas, which are recovered and which can be reused.

One advantage achieved by the method of the invention is also that the biogas produced thereby contains considerably less carbon dioxide than the biogas produced by the conventional methods. A biogas low in carbon dioxide is environmentally friendly.

The method and equipment of the invention have an advantage that when buffer-compound-containing sludge formed in the second reactor is recycled to the first reactor the process stabilizes, because variations in the pH decrease. In conventional reactors of hydrolysis processes the most favourable conditions for the microbes prevail at the bottom of the reactor. In conventional processes, the conditions in the mid-sections of the reactors are reasonably good for the microbes and the conditions in the top layers of the mass in the reactor are poor for the microbes to function. Mixing the mass to be hydrolyzed in the reactor only makes the conditions worse for the microbes in the conventional hydrolysis processes. Instead, the method of the present invention provides optimal conditions for the microbes to function, because the formed buffer compound prevents variations in the pH in the hydrolysis reactor. Thus, the stabilization of the process results in improved processing conditions and larger mass of useful microbes in the hydrolysis reactor. The larger mass of useful microbes, in turn, has a consequence that larger amounts of organic material can be fed into the hydrolysis reactor, or correspondingly, if the same feed quantities are used, the processing time becomes shorter.

The method of the present invention also has an advantage that the buffer compound can be produced from the constituents of the hydrolysis process alone, and there will be no need to add chemicals to the process. Formation of the buffer compound in the second reactor, in a so-called accelerator or stabilizer, is a very economical way to improve and speed up the hydrolysis process. If a commercially available buffer compound were added directly to the first hydrolysis reactor, it should be added in huge quantities and the processing costs would rise unreasonably.

The method and equipment of the present invention enable particularly effective production of particularly pure biogas. The method of the invention provides biogas having high methane content, because the $CO_2$ contained in the biogas fed into the second reactor reacts with ammonia and forms a buffer compound or buffer compounds. Thus, the biogas is washed in the second reactor and no separate biogas washing unit is needed in the hydrolysis installation.

BRIEF DESCRIPTION OF THE DRAWINGS

The invention will be described in greater detail in connection with preferred embodiments, with reference to the attached drawings, FIG. 1 and FIG. 2, which are schematic views of the implementation of some embodiments of the invention.

FIG. 1 shows equipment for implementing a preferred embodiment of the invention.

FIG. 2 shows equipment for implementing a preferred embodiment of the invention.

DETAILED DESCRIPTION OF THE INVENTION

The invention relates to a method for processing organic material, which method employs at least two reactors and comprises the steps of
  a) performing a bioconversion on the organic material in at least one first reactor;
  b) treating the biogas formed in the bioconversion with ammonia in at least one second reactor; and
  c) recycling buffer solution formed in the second reactor to the bioconversion in the first reactor.

In this connection the bioconversion refers to hydrolysis, which is performed partly or completely on organic material. The bioconversion can be a pressurized or an unpressurized process.

The first reactor refers to a reactor or reactors that process the bioconversion. There can be a plurality of reactors processing the bioconversion.

The second reactor refers to a reactor or reactors, into which there is fed partly or completely hydrolyzed organic material and/or ammonia and/or ammonia-containing material and biogas. In fact, this reactor can be considered a kind of accelerator, which speeds up the bioconversion process in the first reactor.

The reactors can be any reaction vessels or containers, or they can be mere pipe sections. A person skilled in the art is able to design suitable reactors to meet the needs of each particular installation.

Organic material is fed into a bioconversion process reactor. The pressure in the process reactor is above the atmospheric pressure or the normal atmospheric pressure. As the organic material decomposes, biogas containing $CH_4$ and $CO_2$ will be produced. The produced biogas is passed through at least one second reactor, which contains ammonia or strongly ammoniacal organic material, whereby the carbon dioxide in the mixed methane/carbon dioxide gas reacts with the ammonia forming a buffer compound or buffer compounds, such as ammonium bicarbonate and/or ammonium carbonate. In the second reactor there are produced buffer compounds or buffer-compounds-containing sludge that can be recycled into the first bioconversion reactor. There may be a plurality of bioconversion process reactors. Also, there may be a plurality of reactors containing ammonia or ammoniacal material.

The reactor or the reactors after the main reactor, in which reactors the buffer compound is produced, are pressurized. Advantageously the pressure is at least about 1.8 bar.

In the second reactor there is thus formed the buffer compound, whereby acid or base additions do not cause considerable changes in the pH and the conditions are optimal for the microbes to function. The formed buffer compounds can be any compounds having buffer properties.

When the pH values in the reactor(s) containing ammonia have been brought to the same level as those in the reactor processing the bioconversion, it is possible to feed the organic material from the second reactor back to the first processing reactor. The reactors after the main reactor, which contain ammonia, yield washed biogas, whose $CO_2$ content is thus lower than in the biogas introduced into the reactors.

In the literature there are several references to the toxicity of ammonia. Previously, ammonia content of 3000 mg/l was regarded as toxic and ammonia content of 1500 to 3000 as inhibiting. Now, it has been surprisingly found, however, that the ammonia content of the material to be treated may be considerably higher and bioconversion takes place nevertheless. As it can be seen from the examples of the present document, the ammonia content of the mass to be hydrolysed is more than three times higher than what was previously considered an inhibition limit.

The pressurized second reactor produces ammonium bicarbonate, because two gases, ammonia and carbon dioxide (dissociated to $NH_4+$ and $HCO_3$ ions), tend to achieve as small a space as possible. Thus, a reactant ammonium ion binds to a carbonic acid ion to obtain ammonium bicarbonate or ammonium carbonate, depending on the amount of free ammonia in the reaction solution. Both of these salts act as buffers with the free ammonia as well as the carbonic acid at the mutual ration of 1:10. Because the living conditions of anaerobic microbes depend to a great extent on the amount of free ammonia and the pH, in other words, as the pH rises the vital functions of the microbes become weaker, the presence of a buffer is extremely advantageous, particularly in feeds having high dry matter content and materials that have already produced ammonia aerobically. Also, carboxyl acids, such as acetic acid, propionic acid or valerianic acid, formed in the bioconversion or existing in the organic material, form a buffer with the free ammonia. Pressure contributes to the formation of buffers, and thus, the second reactor is advantageously pressurized.

The organic material to be processed by the method of the invention can be preserved in acidic or basic conditions prior to being fed into the reactor. This means that the material to be introduced to bioconversion is hygienized prior to the bioconversion.

In the method of the present invention, the bioconversion to be performed can be mesophilic or thermophilic. In this connection the term mesophilic denotes that the bioconversion is performed at a temperature below 40° C. The term thermophilic denotes in this connection that the bioconversion is performed at a temperature of 40 to 70° C., advantageously 55 to 65° C. The conventional thermophilic bioconversion has typically been difficult to manage, but the method of the invention allows easy implementation of the thermophilic bioconversion.

For instance, the method of the invention makes it possible that storage and transport conditions of fish obtained by biomanipulation do not cause extra costs as regards preservability, temperature, storage time, etc.

In our researches we have found that an addition of ammoniacal waste fractions is most convenient to make in the processing reactor, where the carbon dioxide production has already started. It is also advantageous to apply the produced gas from the bottom of the reactor through the reaction solution to carry out mechanical mixing and to complete the carbon dioxide and ammonia reaction as fully as possible.

When ammonium nitrogen fertilizers are prepared, the carbon dioxide is released from the carbonates with an acid, for which purpose the most environmentally friendly and the most viable for our recycling idea is an acetic acid obtained from sugars of plant waste fractions by acetic acid fermentation, whereby the ammonium bicarbonate is modified to ammonium acetate and the released carbon dioxide is conducted to greenhouses or it is stored in some other way, for instance by pressurizing. Instead of the acetic acid, it is also possible to use phosphoric acids, occurring as problem waste, and nitric acid, whose valuable phosphates and nitrates, which are useful for fertilizers, would thus be utilized.

The organic material is material of animal origin, such as fish or fish waste, fowl or fowl waste, material of plant origin, such as cereal, cultivated plant or cultivated plant waste, e.g. barley, cabbage, potato or potato peel. The organic material can also be material of microbial origin, such as yeast or yeast waste, e.g. genetically manipulated yeast waste. The organic material can also be a mixture of the above-described materials.

The bioconversion can be carried out at a pressure above the atmospheric pressure, for instance at a pressure of about 1.2 to 6 bar, advantageously at a pressure of 2 to 4 bar. The bioconversion can also be carried out at normal atmospheric pressure. Advantageously, the bioconversion is pressurized.

The bioconversion is carried out by means of microorganisms present in the organic material and/or by means of added microorganisms.

The method employs at least two reactors, whereby one is used for bioconversion and the other for cleaning the biogas. The other reactor, where the biogas is cleaned, contains organic material, ammonia or a mixture of organic material and ammonia. The method of the invention is advantageously implemented as continuous circulation.

In the method the ammonia is produced in the hydrolysis of the organic material. To the first reactor, where the bioconversion takes place, is added a buffer solution from the second reactor. Optionally, it is also possible to add organic, partly hydrolyzed material to the bioconversion reactor.

The buffer solution resultant from the ammonia and carbon dioxide reaction contains ammonium bicarbonate and/or ammonium carbonate and free ammonia and/or carbonic acid. The ratio between the ammonium bicarbonate or ammonium carbonate and the free ammonia and/or the carbonic acid is 1:10.

The hydrolyzed product obtained from the organic material by the method can be recovered and it can be utilized, for instance, as a soil conditioner, fertilizer or a fertilizer-like product or as a repellent.

The cleaned biogas is also advantageously recovered and it can be used as a greenhouse gas, for heating, for electricity production or as a fuel. The cleaned biogas contains carbon dioxide less than 25%, generally it contains 15 to 20% carbon dioxide.

The invention also relates to a hydrolyzed product, which is prepared by the method, in which bioconversion is performed on organic material, the resultant biogas is treated with ammonia, the produced buffer solution or sludge is recycled to the bioconversion and the obtained hydrolysis product is recovered.

The invention also relates to a cleaned biogas, which is prepared by the method, in which bioconversion is performed on organic material, the resultant biogas is treated with ammonia, the produced buffer solution or sludge is recycled to the bioconversion and the cleaned biogas is recovered.

The products obtained by the method of the invention are purer than the previously prepared products and all the products produced in the method can be utilized. For instance, the biogas produced and washed by the method of the invention contains considerably less $CO_2$ than the biogas produced by conventional methods.

The invention also relates to equipment for processing organic material. FIG. 1 shows equipment for implementing one embodiment of the invention. The reference numeral 1 denotes pressure gauges, which are intended for regulating the pressure and moving the mass. Gas cleaning starts in pre-processing, by which the material can be subjected to higher pressure than in the main reactor, which enables sludge transfers from one reactor to the other. The reference numeral 2 denotes the incoming, suspended ammoniacal material. The reference numeral 3 denotes a mixed gas nozzle, through which $CO_2$ is dissolved in the material. The reference numeral 4 denotes the material that has reached a buffer. The reference numeral 5 denotes a mixture of $CH_4$/$CO_2$ conveyed from the main reactor to the gas cleaning. The reference numeral 6 denotes washed, outlet $CH_4$. The reference numeral 7 denotes the finished end product from the main reactor, which product is used for soil conditioning.

One example of the equipment of the invention is described in FIG. 2. The equipment for processing organic material comprises at least one first reactor 9, at least one second reactor 10, a pipe 12 for transferring the organic material to be processed from the at least one first reactor 9 to the at least one second reactor 10, a pipe 14 for transferring the biogas from the at least one first reactor 9 to the at least second reactor 10, a pipe 15 for recycling the buffer-compound-containing material from the at least one second reactor 10 to the at least one first reactor 9. Alternatively, the pipes 12 and 14 may start directly from the first reactor 9 and be connected to the second reactor 10. The equipment also comprises a pipe 8 for introducing the organic material into the first reactor 9, a pipe 13 for removing the biogas from the first reactor 9 and a pipe 11 for removing the partly or completely hydrolyzed product from the first reactor 9.

The first reactor refers here to a reactor or reactors processing the bioconversion. The reactor(s) may be pressurized or they may be at normal atmospheric pressure.

The second reactor refers here to a reactor or reactors, into which is introduced partly hydrolyzed organic material and/or ammonia and/or ammonia-containing material and biogas. In fact, this reactor can be considered a kind of an accelerator, which speeds up the bioconversion process in the first reactor.

In the following, the operation of the equipment will be described in greater detail. Organic material is introduced into the first reactor 9 via a pipe 8. In the first reactor 9, bioconversion takes place and biogas starts forming. From the first reactor 9 it is possible to remove partly or completely hydrolyzed organic material via a pipe 11. From the pipe 11 departs a branch pipe 12, through which partly or completely hydrolyzed product is transferred into the second reactor 10. Biogas formed in the first reactor 9 is removed via a pipe 13. From the pipe 13 departs a branch pipe 14, through which biogas is transferred to the second reactor 10, where the biogas and the partly or completely hydrolyzed organic material, which contains ammonia, form a buffer compound or buffer compounds. Alternatively, the branch pipes 12 and 14 may connect the first reactor 9 directly to the second reactor 10. The first reactor 9 may be pressurized or at normal pressure. The second reactor 10 is pressurized, advantageously the pressure is at least 2 bar. Buffer-compound-containing sludge or solution formed in the second reactor 10 is transferred via a pipe 15 back to the first reactor 9.

It is apparent to a person skilled in the art that as technology progresses the basic idea of the invention can be implemented in a variety of ways. Thus, the invention and its embodiments are not restricted to the above-described examples, but they may vary within the scope of the claims.

EXAMPLES

Example 1

Processing of Organic Material and Generation of Biogas

To a reactor R1 having a capacity of 300 liters was introduced organic material that contained 18.8 kg bone flour, 28.9 kg fish and 3.8 kg genetically manipulated yeast (Genencor) and 20 liters inoculum, which contained own microbes of different fishes and yeast. The pressure in the reactor was 2 bar. The pH in the reactor was 8.2. The total $NH_4$ content was determined with a spectrophotometer and it was 9200 mg/l. In addition, the amount of carbonates was determined by means of sulphuric acid and the ammonium ion content as ammonium carbonate was calculated therefrom. The ammonium ion content was calculated to be 8700 mg/l and the content of carbonates was 46300 mg/l. The alkalinity and phosphate content were also determined. The alkalinity was 32000 and the phosphate content was 1200 mg/l. The amount and composition of the biogas obtained from the reactor were measured. On the following day, the reactor yielded 109.4 l/day of biogas, containing 74.6% $CH_4$ and 20.0% $CO_2$.

The biogas obtained from the reactor R1 can be further introduced into a reactor, which contains highly ammoniacal biowaste and in which the carbon dioxide further reacts with the ammonia forming a buffer compound. The toxicity of the ammonia then disappears and the conditions will be optimal for microbes.

Example 2

Processing of Organic Material and Generation of Biogas

To a reactor R4 having a capacity of 250 liters was introduced organic material that contained 6.2 kg bone flour, 24.15 kg fish and 3.92 kg genetically manipulated yeast (Genencor) and 20 liters inoculum, which contained own microbes of different fishes and yeast. The pressure in the reactor was 2 bar. The pH in the reactor was 8.0. The total $NH_4$ content was determined with a spectrophotometer and it was 5800 mg/l. In addition, the amount of carbonates was determined by means of sulphuric acid and the ammonium ion content as ammonium carbonate was calculated therefrom. The ammonium ion content was calculated to be 7400 mg/l and the content of carbonates was 39400 mg/l. The alkalinity and phosphate content were also determined. The alkalinity was 21000 and the phosphate content was 1100 mg/l. The amount and composition of the biogas obtained from the reactor were measured. On the following day, the reactor yielded 140 l/day of biogas, containing 76.8% $CH_4$ and 17.4% $CO_2$.

Example 3

Verification of the Buffer Property of the Organic Material in the Reactor with Sulphuric Acid Additions From the reactor R(4) there was taken a 50 ml sample of organic material during the process. In order to verify a buffer property the pH of the sample was measured and thereafter 1-% $H_2SO_4$ was added thereto. Prior to the acid addition, the pH of the sample was 7.6.

TABLE 1

| Addition 1-% $H_2SO_4$, ml | PH |
|---|---|
| 0.5 | 7.6 |
| 1 | 7.5 |
| 2 | 7.4 |
| 3 | 7.3 |
| 4 | 7.3 |
| 5 | 7.1 |
| 6 | 7.1 |
| 7 | 7.0 |
| 8 | 6.9 |
| 9 | 6.9 |
| 10 | 6.9 |

The pH of the distilled water was 7.6. To 50 ml of distilled water was added 0.5 ml 1-% $H_2SO_4$, whereby the pH dropped to 2.3. The buffer effect is thus clearly apparent.

Example 4

Verification of the Buffer Property of the Organic Material in the Reactor with Ammonia Additions From the reactor R(4) there was taken a 50 ml sample of organic material. In order to verify a buffer property the pH of the sample was measured and thereafter 1-% $NH_3$ was added thereto. Prior to the base addition the pH of the sample was 7.6.

TABLE 2

| Addition 1-% $NH_3$, ml | PH |
|---|---|
| 0.5 | 7.8 |
| 1 | 7.9 |
| 1.5 | 8.0 |
| 2 | 8.1 |
| 3 | 8.3 |
| 4 | 8.4 |
| 5 | 8.5 |
| 6 | 8.6 |
| 7 | 8.6 |
| 8 | 8.7 |
| 9 | 8.8 |
| 10 | 8.9 |

The pH of the distilled water was 7.7. To 50 ml of distilled water was added the following amounts of 1-% $NH_3$ and the changes in the pH were measured.

TABLE 3

| Addition 1-% $NH_3$, ml | PH |
|---|---|
| 0.5 | 7.8 |
| 0.1 | 9.7 |
| 1 | 9.9 |
| 2 | 10.1 |
| 3 | 10.2 |
| 4 | 10.2 |
| 5 | 10.3 |
| 10 | 10.5 |

These results also show clearly that the washing of biogas according to the invention provides a powerful buffer effect and thereby improves the functioning conditions of the microbes that degrade the material.

Example 5

Verification of Carbonate Content of the Hydrolysis Product and the Material in the Reactor A thermal cupboard test was performed on the hydrolysis product obtained from the reactor R(4). A thermal cupboard test was also performed on the ammonium hydrocarbonate. Each sample was allowed to rest at a designated temperature in the fume cupboard for about half an hour. Thereafter, sample was placed on top of sulphuric acid. If strong effervescence occurred, it implied that the sample still contained carbonate. In Table 4 effervescent samples are indicated by the sign+.

TABLE 4

| Temperature/° C. | R(4) | $NH_4HCO_3$ |
|---|---|---|
| 50 | + | + |
| 60 | + | + |
| 80 | + | + |
| 100 | + | + |

It was also found that when the sample containing 30000 mg/l ammonium carbonate was allowed to rest at room temperature for one week, after the week there was still 13000 mg/l ammonium carbonate left in the sample.

Correspondingly, in the sample from the reactor R(4) there was initially 29000 mg/l ammonium carbonate and after allowing it to rest at room temperature for a week there was 10000 mg/l carbonate.

Example 6

Verification of a Buffer Property of a Completely Hydrolyzed Product

To the reactor R8 was introduced 20 kg fish, 5 kg inoculum, which contained own microbes of different fishes and yeast, 1 kg genetically manipulated yeast waste (Genencor) and 95 kg water. The pressure in the reactor was 2 bar. Hydrolysis was carried out in the reactor. From the reactor R8 were taken two 100 ml samples of fully processed fish-based hydrolysis residue. The dry solids content of the hydrolysis residue was 5%. Carbon dioxide content was measured with sulphuric acid addition, which was used for calculating the ammonium carbonate content 27900 mg/l. This corresponds to 5200 mg/l ammonia.

The buffer effect of the samples taken from the reactor was first verified by adding 2.5-percent ammonium hydroxide to the first sample and then by adding 2.5-percent acetic acid to the second sample. The tables also show the effect of the ammonium hydroxide or acetic acid addition on the pH of water. The results are shown in Tables 5 and 6 below.

TABLE 5

| $NH_4OH$ addition/ml | pH in R8 sample | pH in water |
|---|---|---|
| 0 | 8.15 | 8.13 |
| 0.5 | 8.26 | 10.52 |
| 1 | 8.35 | 10.74 |
| 1.5 | 8.44 | 10.87 |
| 2 | 8.51 | 10.96 |
| 2.5 | 8.57 | 11.02 |
| 3 | 8.62 | 11.09 |
| 4 | 8.72 | 11.16 |
| 5 | 8.8 | 11.22 |
| 6 | 8.87 | 11.30 |
| 7 | 8.93 | |
| 8 | 8.98 | 11.39 |
| 9 | 9.03 | |
| 10 | 9.07 | |
| 15 | 9.25 | 11.5 |
| 20 | 9.38 | |
| 25 | 9.48 | 11.61 |
| 30 | 9.56 | |

TABLE 6

| Acetic acid addition/ml | pH in R8 sample | pH in water |
|---|---|---|
| 0 | 8.15 | 8.13 |
| 1 | 8.13 | 4.78 |
| 1.5 | 8.09 | 4.31 |
| 2 | 8.05 | 4.1 |
| 2.5 | 8.01 | 3.97 |
| 3 | 7.96 | 3.87 |
| 4 | 7.87 | 3.8 |
| 5 | 7.78 | 3.69 |
| 6 | 7.67 | 3.61 |
| 7 | 7.57 | |
| 8 | 7.46 | |
| 9 | 7.35 | |
| 10 | 7.31 | 3.38 |
| 20 | 6.96 | 3.19 |
| 25 | 6.87 | |
| 30 | 6.74 | |
| 40 | 6.56 | 3 |
| 50 | 6.38 | |

Example 7

To the reactor R6 was introduced 30 kg fish, 7.5 kg inoculum, which contained own microbes of different fishes and yeast, 1.5 kg genetically manipulated yeast waste (Genecor) and 142.5 kg water. The pressure in the reactor R6 was normal atmospheric pressure. To the reactor R8 was introduced 20 kg fish, 5 kg inoculum, which contained own microbes of different fishes and yeast, 1 kg genetically manipulated yeast waste (Genencor) and 95 kg water. The pressure in the reactor R8 was 2 bar. Hydrolysis was carried out in both reactors. After the hydrolysis, five solution samples were taken from both reactors, the samples were filtered and measured for the ammonium content spectrophotometrically. The ammonium carbonate content was determined by means of sulphuric acid and methyl red, and on the basis of the amount of ammonium carbonates the $NH_4^+$ content was also calculated. The results are shown in Table 7. The ammonium content calculated from the ammonium carbonate may be smaller than the measured ammonium content. A likely reason for this is that the ammonium ion content is measured from the filtered solution and the ammonium carbonate content from the unfiltered solution.

TABLE 7

| Sample | Reactor | $NH_4^+$/ mg/l | Carbonates mg/l | $NH_4^+$/ calculated | pH |
|---|---|---|---|---|---|
| 1 | R6 | 3200 | 7000 | 1300 | 6.7 |
| 1 | R8 | 2700 | 6000 | 1100 | |
| 2 | R6 | 2400 | 4200 | 800 | 7.2 |
| 2 | R8 | 2500 | 4200 | 800 | 6.6 |
| 3 | R6 | 3000 | 12000 | 2200 | 7.7 |
| 3 | R8 | 7900 | 32100 | 6000 | 8.2 |
| 4 | R6 | 3100 | 13700 | 2600 | 7.4 |
| 4 | R8 | 4000 | 35600 | 6700 | 7.8 |
| 5 | R6 | 1900 | 17100 | 3000 | 7.4 |
| 5 | R8 | 5500 | 42900 | 8000 | 8.1 |

Example 8

Production of Biogas

To the reactor R1 having a capacity of 300 liters was introduced organic material, which contained 18.8 kg bone flour, 28.9 kg fish and 3.8 kg genetically manipulated yeast waste (Genencor) and 20 liters inoculum, which contained own microbes of different fishes and yeast. In addition there was 275 kg water in the reactor. The pressure in the reactor was 2 bar. Hydrolysis was carried out in the reactor. Part of the mass in the hydrolysis reactor R1 was moved into a second reactor, into which was also fed biogas generated in the first reactor. In the second reactor a buffer compound or a mixture of buffer compounds was formed under pressure, and the sludge in the second reactor was recycled back to the first reactor. The amount of produced biogas was measured and its methane and carbon dioxide contents were assayed. The ammonium ion content of the hydrolyzed mass was measured spectrophotometrically. The mass was also measured for the ammonium bicarbonate content and that was used for calculating the ammonium ion content. The test was repeated five times. The results are shown in Table 8.

TABLE 8

| Sample | $CH_4$/ % | $CO_2$/ % | Biogas/ l/day | $NH_4^+$ measured mg/l | $NH_4^+$ calculated mg/l | Carbonate mg/l | pH |
|---|---|---|---|---|---|---|---|
| 1 | 73.6 | 22.8 | 118 | 9700 | 8000 | 42900 | 7.8 |
| 2 | 70.6 | 24.6 | 136.8 | | | | |
| 3 | 71.4 | 23.6 | 132 | | | | |
| 4 | 69.6 | 25.6 | 122 | | | | |
| 5 | 72.4 | 25 | 72 | 7200 | 10000 | 53600 | 7.8 |

Example 9

Production of Biogas

A test corresponding to that performed in the reactor R1 was also performed in the reactor R4 three times. To the reactor R4 having a capacity of 250 liters was introduced organic material containing 6.2 kg bone flour, 24.15 kg fish and 3.92 kg genetically manipulated yeast waste (Genencor) as well as 20 liters inoculum containing own microbes of different fishes and yeast. There was 225 liters of water in the reactor. The pressure in the reactor was 4 bar. The results are shown in Table 9.

TABLE 9

| Sample | $CH_4$/% | $CO_2$/% | Biogas/ l/day | $NH_4^+$ measured mg/l | $NH_4^+$ calculated mg/l | Carbonate mg/l |
|---|---|---|---|---|---|---|
| 1 | 72.8 | 20.2 | 360 | | | |
| 2 | 71.4 | 23.6 | 122 | 4800 | 6800 | 36400 |
| 3 | 72.2 | 22.8 | | 5100 | 8000 | 42900 |

Example 10

Verification of Thermal Resistance of Hydrolyzed Product

From the reactor R8 there was taken a sample, which was kept in a closed container in a thermal cupboard at a temperature of 68 to 70° C. The cooled solution was assayed for ammonium carbonate content, which was exactly the same as in the unfermented reactor R8, i.e. 31700 mg/l. Calculated as ammonia, it corresponds to the value 5900 mg/l ($NH_4^+$). This test indicates that the buffer effect remains in the material, even though it is heated to the temperature of 68 to 70° C.

The invention claimed is:

1. A method for processing organic material to produce a hydrolysed product and a cleaned biogas, wherein the method employs at least two reactors and comprises the steps of
   a) performing a bioconversion on the organic material in the first reactor;
   b) treating the biogas formed in the bioconversion with ammonia in the second reactor which is pressurized; and
   c) recycling buffer solution formed in the second reactor to the first reactor.

2. A method as claimed in claim 1, wherein the organic material is material of animal origin.

3. A method as claimed in claim 2, wherein the organic material is fish or fish waste, fowl or fowl waste.

4. A method as claimed in claim 1, wherein the organic material is material of plant origin.

5. A method as claimed in claim 4, wherein the organic material is a cultivated plant or cultivated plant waste, such as cabbage, potato or potato peel.

6. A method as claimed in claim 1, wherein the organic material is material of microbial origin, such as yeast or yeast waste.

7. A method as claimed in claim 1, wherein the bioconversion is a pressurized process.

8. A method as claimed in claim 1, wherein the bioconversion is carried out at pressure, which is over the atmospheric pressure.

9. A method as claimed in claim 8, wherein the bioconversion is carried out at a pressure of about 1.2 to 6 bar, advantageously at a pressure over 2 bar.

10. A method as claimed in claim 1, wherein the bioconversion is an unpressurized process.

11. A method as claimed in claim 10, wherein the pressure in the second reactor is over 1.8 bar.

12. A method as claimed in claim 1, wherein the organic material is stored in acidic conditions prior to carrying out the bioconversion.

13. A method as claimed in claim 1, wherein the organic material is stored in basic conditions prior to carrying out the bioconversion.

14. A method as claimed in claim 1, wherein the bioconversion is mesophilic.

15. A method as claimed in claim 1, wherein the bioconversion is thermophilic.

16. A method as claimed in claim 1, wherein the bioconversion is carried out by means of microorganisms existing in the organic material.

17. A method as claimed in claim 1, wherein the bioconversion is carried out by means of added microorganisms.

18. A method as claimed in claim 1, wherein the bioconversion is carried out in anaerobic conditions.

19. A method as claimed in claim 1, wherein at least two reactors are employed, whereby one is used for the bioconversion and the other is used for biogas cleaning.

20. A method as claimed in claim 19, wherein the reactor, where the biogas is cleaned, contains organic material.

21. A method as claimed in claim 19, wherein the reactor, where the biogas is cleaned, contains ammonia.

22. A method as claimed in claim 19, wherein the reactor, where the biogas is cleaned, contains a mixture of organic material and ammonia.

23. A method as claimed in claim 22, wherein the ammonia was produced in the hydrolysis of the organic material.

24. A method as claimed in claim 1, wherein to the first reactor, where the bioconversion takes place, is added buffer solution and, optionally, organic, partly hydrolyzed material from the second reactor.

25. A method as claimed in claim 1, wherein the formed buffer solution contains ammonium bicarbonate or ammonium carbonate and free ammonia and/or carbonic acid.

26. A method as claimed in claim 25, wherein the formed buffer solution contains ammonium bicarbonate or ammonium carbonate and free ammonia and/or carbonic acid at the ratio of 1:10.

27. A method as claimed in claim 1, wherein the hydrolyzed product obtained from the organic material in the method is recovered.

28. A method as claimed in claim 1, wherein the cleaned biogas is recovered.

29. Equipment for processing organic material according to a method of claim 1, wherein the equipment comprises at least one first reactor, at least one second reactor, a pipe for transferring the organic material to be processed from the at least one first reactor to the at least one second reactor, a pipe for transferring biogas from the at least one first reactor to the at least one second reactor, a pipe for recycling buffer-compound-containing material from the at least one second reactor back to the at least one first reactor.

30. Equipment as claimed in claim 29, also comprising a pipe for introducing the organic material into the first reactor, a pipe for discharging the biogas from the first reactor and a pipe for removing the partly or completely hydrolyzed product from the first reactor.

31. Equipment as claimed in claim 29, wherein the bioconversion of the organic material takes place in the first reactor and a buffer compound or buffer compounds are formed in the second reactor.

32. Equipment as claimed in claim 29, wherein the reactors comprise at least one of vats, containers and pipes.

33. Equipment as claimed in claim 30, wherein the reactors comprise at least one of vats, containers and pipes.

* * * * *